United States Patent [19]
Manoukian et al.

[11] Patent Number: 5,304,172
[45] Date of Patent: Apr. 19, 1994

[54] FIBER OPTIC PROBE

[75] Inventors: Nubar Manoukian, Sunnyvale; Kalman Kele, Scotts Valley; James R. Kermode, Sunnyvale, all of Calif.

[73] Assignee: Coherent, Inc., Palo Alto, Calif.

[21] Appl. No.: 16,768

[22] Filed: Feb. 11, 1993

[51] Int. Cl.$^5$ .......................................... A61B 5/0215
[52] U.S. Cl. ....................................... 606/15; 606/14; 606/16; 385/60
[58] Field of Search ....................... 606/2, 3, 7, 13-17, 606/27, 28; 128/395-398

[56] References Cited

U.S. PATENT DOCUMENTS

| | | | |
|---|---|---|---|
| 3,834,391 | 9/1974 | Block | 606/16 X |
| 4,273,109 | 6/1981 | Enderby | 606/15 |
| 4,503,853 | 3/1985 | Ota et al. | 606/16 |
| 4,895,145 | 1/1990 | Joffe et al. | 606/15 |
| 5,125,058 | 6/1992 | Tenerz et al. | 606/15 |
| 5,219,345 | 6/1993 | Potter | 606/15 |

Primary Examiner—Peter A. Aschenbrenner
Attorney, Agent, or Firm—Limbach & Limbach

[57] ABSTRACT

A fiber optic probe is disclosed for delivering laser radiation from a medical laser system to a treatment site. The probe includes a handpiece having an axial channel. The axial channel includes an intermediate mating region of reduced diameter. A tip piece having a fiber located therein is mounted on the front end of the handpiece. The input end of the fiber is mounted in a ferrule which is received in the reduced diameter mating region of the handpiece. A tail piece which includes an optical fiber is mounted at the rear end of the handpiece. The delivery end of the fiber in the tail piece is mounted in a ferrule and is also received in the mating region of the handpiece. The two ferrules are spring biased together to maximize coupling efficiency. The mating region is spaced from the front end of the handpiece so that the force on the mating region, caused by the torque imparted to the tip piece during use, is less than it would be if the mating region were located at the front end whereby the coupling efficiency is maintained. The handpiece is designed to be reused after sterilization in an autoclave.

25 Claims, 4 Drawing Sheets

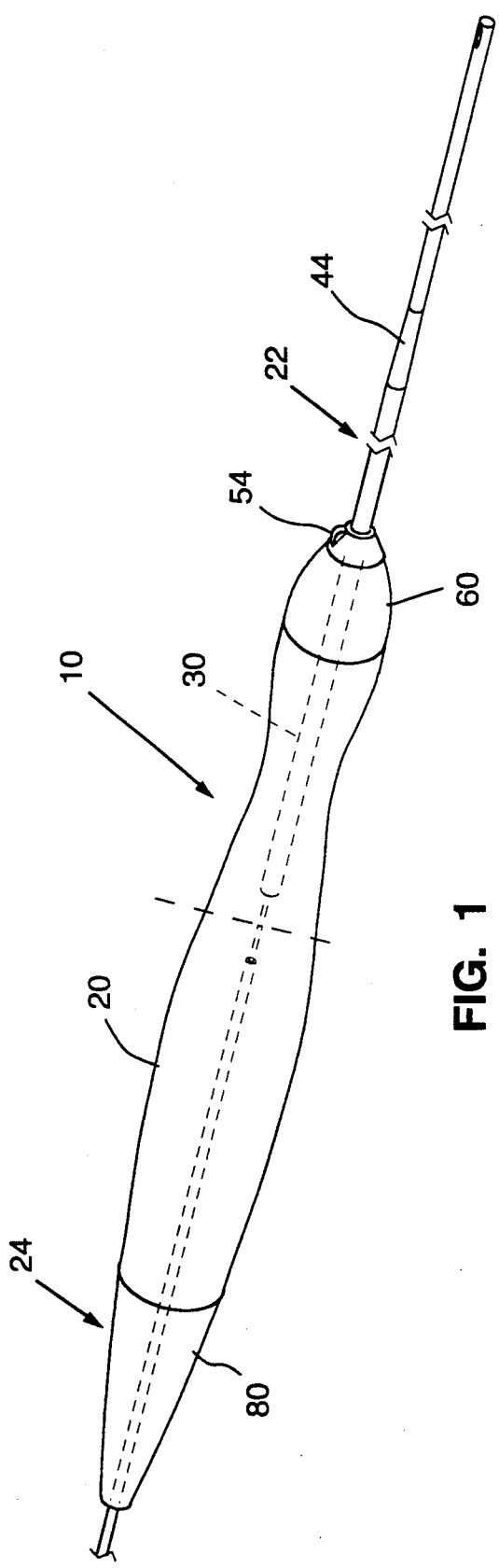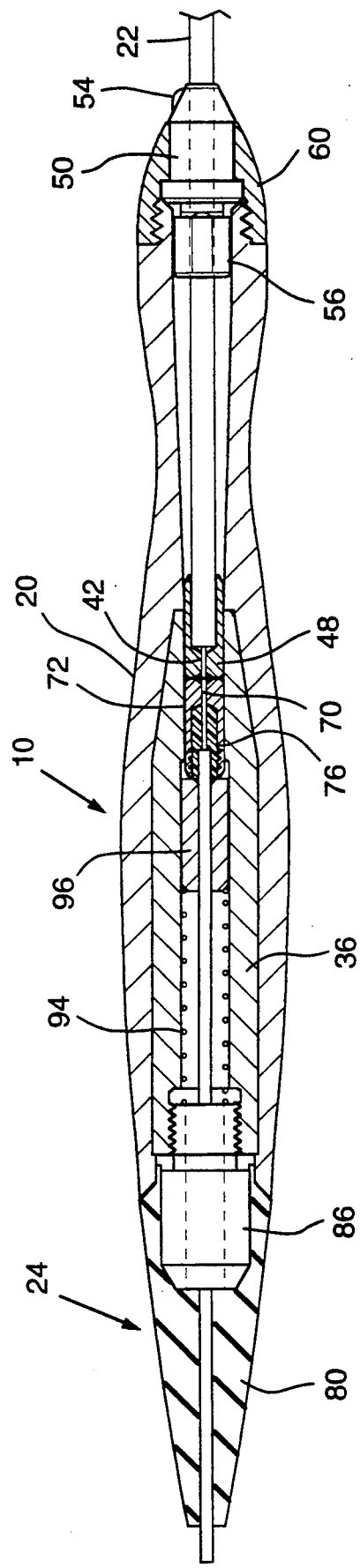

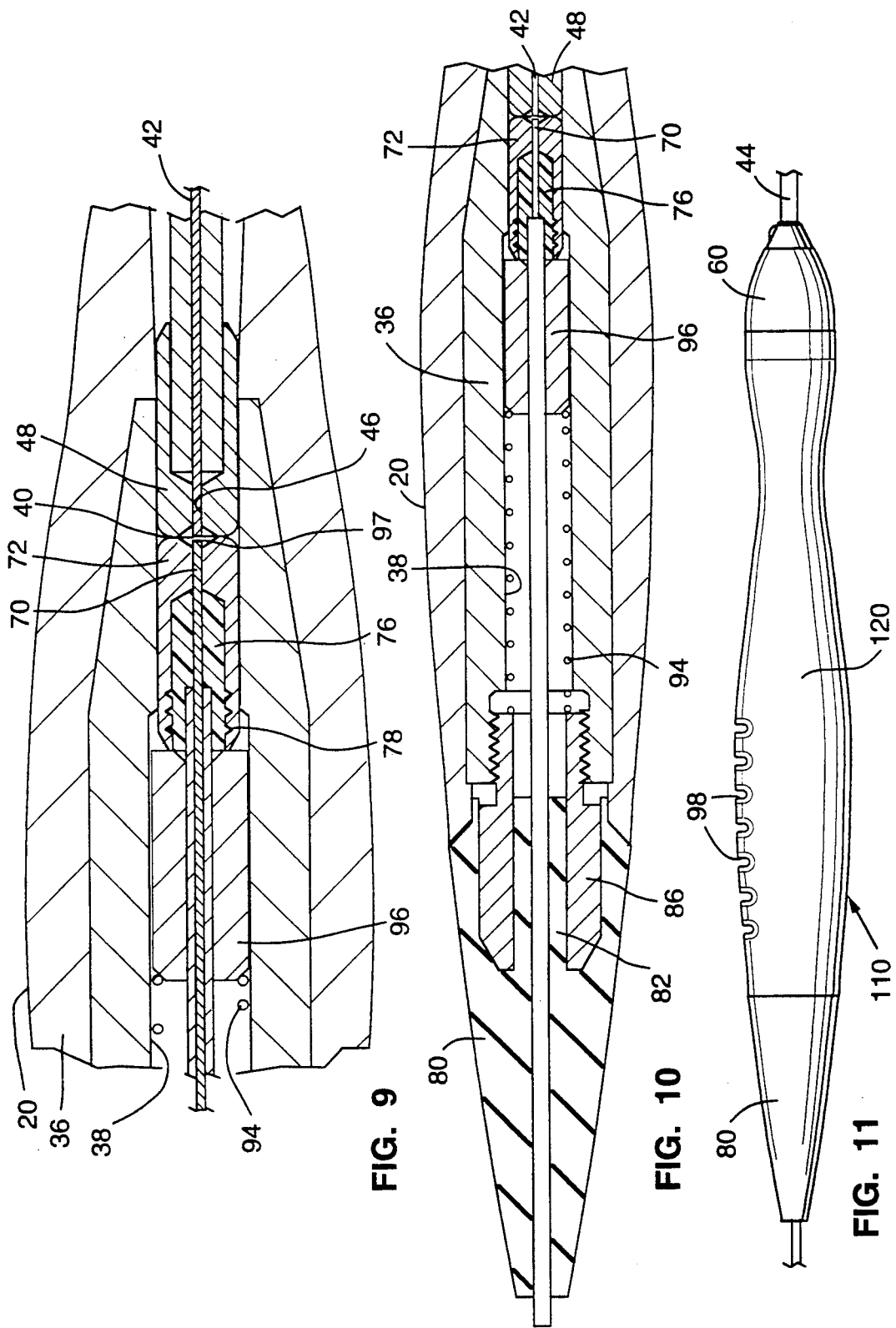

FIBER OPTIC PROBE

TECHNICAL FIELD

The subject invention relates to a fiber optic probe for use in medical procedures. The probe includes a handpiece and a connectable tip.

BACKGROUND OF THE INVENTION

In recent years, there has been a considerable increase in the use of lasers in medicine and surgery. In one class of medical lasers, the laser energy is delivered from the laser to the patient via an optical fiber. Once such laser system which has achieved significant commercial success is marketed by the assignee herein under the trademark Versapulse. The Versapulse system includes a solid state Holmium:YAG laser that generates an output of 30 watts average power at a wavelength of 2.1 microns. The laser energy is coupled through an optical fiber which terminates in a handpiece manipulated by the surgeon.

A laser system of this type is used for a wide variety of surgical applications and is particularly suited for arthroscopic procedures. As the field has grown, a variety of handpieces have been developed which allow the surgeon latitude in treatment approaches. For example, the delivery end of the tip projecting out of the handpiece can be straight or curved. The delivery end of the probe can also include tines to help capture and stabilize cartilage during ablation. At the present time, a surgeon will often desire to use more than one probe configuration during a single procedure.

As can be appreciated, because of the potential for spreading infection, a probe used during one procedure can not be used with another patient in a subsequent procedure unless some form of sterilization was performed. Unfortunately, the probes that were initially introduced to the marketplace were not designed to withstand sterilization procedures and were therefore discarded after a single use.

Since that time, attention has been given to improving the design of the probe so that it can be sterilized. Within the last year, the assignee herein has manufactured and sold probes which could be sterilized using gas techniques. Unfortunately, gas sterilization is a relative time consuming, costly and potentially carcinogenic approach. In contrast, high temperature steam sterilization in an autoclave is faster, safer and less expensive. However, the prior probes were incapable of withstanding the high temperatures encountered in an autoclave. Accordingly, it would be desirable to provide a probe which could be sterilized in an autoclave.

The problems associated with sterilizing probes have been compounded by the proliferation of various tip designs described above. As can be appreciated, if a surgeon desires to use two or three different probes with different tip designs in a single procedure, all of the probes would have to be sterilized after use.

One prior art approach which has been implemented to address this difficulty has been to provide a two-part probe. The two-part probe includes a disposable tip piece and a reusable handpiece. During any given procedure, the surgeon can use a single handpiece and change tips (and delivery modalities) depending upon the requirements of the procedure as it progresses. At the end of the procedure, all of the tips that were used are discarded. Only the single handpiece needs to be sterilized.

There are still some difficulties associated with the latter approach which utilizes a two-part probe. First, the handpiece cannot be sterilized in an autoclave and the less desirable gas sterilization must be used. More significantly, since the delivery fiber now consists of two pieces, a means must be provided to insure that the optical coupling between the abutting ends of the fibers is maintained during use. In the prior art system, the disposable tip included a short extension member which projected about one half inch into the handpiece. A threaded coupling secured the tip in place.

The latter approach can provide good optical coupling when the two parts are initially connected. However, during a surgical procedure, the surgeon will push and twist the probe creating a torque on the interconnection between the tip and the handpiece. More specifically, a surgeon will can exert up to about one pound of force on the end of the tip during a procedure. The amount of torque this force generates is dependent on the length of the tip. Since a standard tip is on the order of five inches in length, the torque at the front end of the handpiece would be five inch-pounds.

When this amount of torque is applied to the optical coupling it can cause the ends of the abutting fibers to become misaligned. When the ends of the fibers become misaligned, the energy of the laser will not be coupled from one to the other but rather will scatter within the handpiece. If the leakage is severe, the fiber and/or the handpiece can overheat and be catastrophically destroyed. Even if the leakage is insufficient to cause destruction, the power lost will prevent the desired laser energy level from being delivered to the surgical site.

Accordingly, it would be desirable and is an object of the present invention to design a optical probe which includes a connectable tip having a configuration designed to maintain optical coupling efficiency during a surgical procedure.

It is a further object of the subject invention to provide a handpiece which can be readily sterilized in a steam autoclave.

It is still another object of the subject invention to provide a tip which is either disposable or could be sterilized in a steam autoclave.

SUMMARY OF THE INVENTION

In accordance with the subject invention, a fiber optic probe is provided which includes an elongated handpiece having front and rear ends. An axial channel extends between the ends of the handpiece. The channel includes a reduced diameter mating region spaced from the front end of the handpiece.

The probe further includes a tip piece which is connectable to the front end of the handpiece. The tip piece includes an optical fiber a portion of which is received in the channel of the handpiece. The end of the fiber is mounted within a ferrule which is received in the mating region of the channel.

The probe further includes a tail piece which is connectable to the rear end of the handpiece. The tail piece also includes an optical fiber having an input end which is connected to the laser source and a delivery end received in the channel of the handpiece. The delivery end of the fiber is mounted within a ferrule which is also positioned in the mating region of the channel and in abutting relationship with the ferrule associated with the tip piece.

The subject design functions to maintain a high coupling efficiency even during use. One reason this result is achieved is that the coupling region between the fibers is spaced away from the front end of the handpiece. In this manner, the forces on the coupling region caused by the torque exerted on the tip piece will be less than if the coupling where located at the front of the handpiece. The amount of force experienced at the coupling region is a function of the ratio between the length of the fiber within the handpiece versus the length of the fiber extending beyond the front end of the handpiece. The length of fiber within the handpiece should be at least twenty five percent and preferably about fifty percent of the length of the fiber outside of the handpiece.

Optical coupling between the fibers is further enhanced by configuring the ferrules to fit tightly in the mating region thereby minimizing movement and misalignment. In the preferred embodiment of the subject invention, the ferrules are placed under spring tension, forcing the fibers together to insure maximal optical coupling. In another feature of the preferred embodiment, the end of at least one of the fibers is spaced inwardly from the end of the ferrule. In this manner, there is no direct contact between the ends of the fiber and the integrity of the fibers can be improved. More specifically, it has been found that even if the ends of the fiber are highly polished, some residual features will remain. If the fibers are placed in direct contact, the features will act as point contacts directing all the mating forces to localized regions causing the fiber to fracture. Thus, it is desirable to provide a small space between the ends of the fibers to prevent such fractures.

In another aspect of the invention, the handpiece has been specifically designed to withstand the heat and moisture encountered in a steam autoclave used for sterilization. In this manner, the handpiece does not have to be sterilized with the more costly, time consuming and carcinogenic gas sterilization approach. This result is achieved by selecting the materials forming the handpiece which can withstand the maximum heat which is encountered in an autoclave which would be about 132 degrees centigrade.

In addition to selecting the proper materials, the adhesive connection between the optical fiber and the ferrule is also improved. More specifically, the outer surface of the adhesive and the inner surface of the ferrule are provided with an interlocking configuration. This interlocking configuration prevents the fiber from separating from the ferrule as the elements expand and contract during the heating cycle in the autoclave.

In the preferred embodiment, the tip piece is also designed to be sterilized using a steam autoclave. In addition to the proper selection of materials, only the delivery end of the fiber is adhesively secured to an outer tubular support member. This approach accommodates the difference in expansion between the fiber and the outer support member during the temperature cycling in an autoclave.

In practice, the tips are often damaged when used on hard tissue. By having a separate tip piece, the surgeon can chose to discard a damaged tip piece and avoid the cost of replacing the entire probe.

Further objects and advantages of the subject probe will become apparent from the following detailed description taken in conjunction with the drawings in which:

BRIEF DESCRIPTION OF THE DRAWINGS

FIG. 1 is a perspective view of the fiber optic probe of the subject invention.

FIG. 2 is a cross sectional view of the probe of the subject invention.

FIG. 9 is an enlarged, cross sectional view of the mating region of the handpiece illustrating the abutting ferrules.

FIG. 10 is an enlarged, cross-sectional view of the rear end of the handpiece and illustrating the spring loading of the ferrules.

FIG. 11 is an alternate embodiment of the shell of the handpiece which includes venting structures to aid in heat dissipation.

DETAILED DESCRIPTION OF THE PREFERRED EMBODIMENTS

Figures 3, 4:
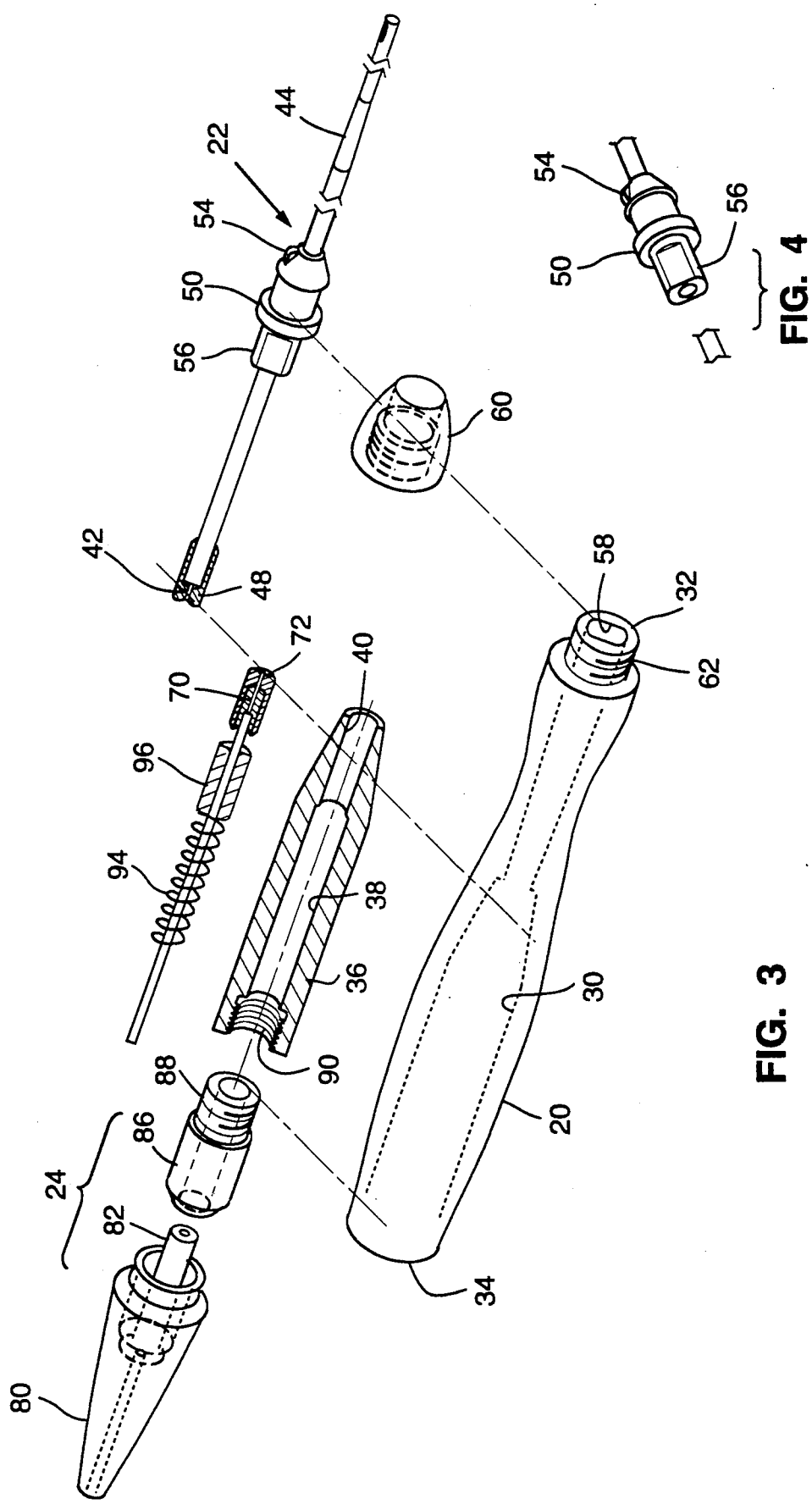
FIG. 3 is an exploded perspective view of the probe of the subject invention.
FIG. 4 is a perspective view of the coupler used to connect the tip piece of the probe to the handpiece.
Figure 6:
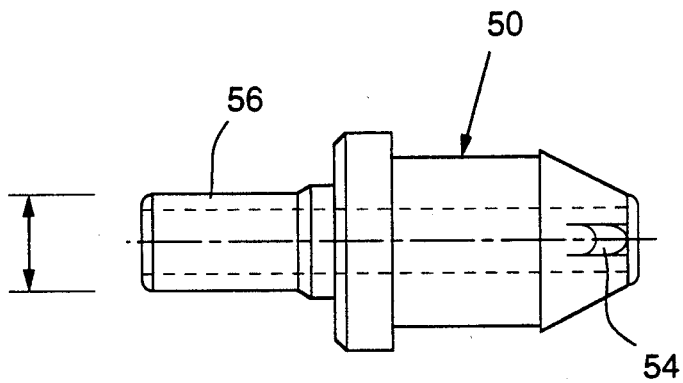
FIG. 6 is a side elevational view of the coupler used to connect the tip piece of the probe to the handpiece.
Figure 5:
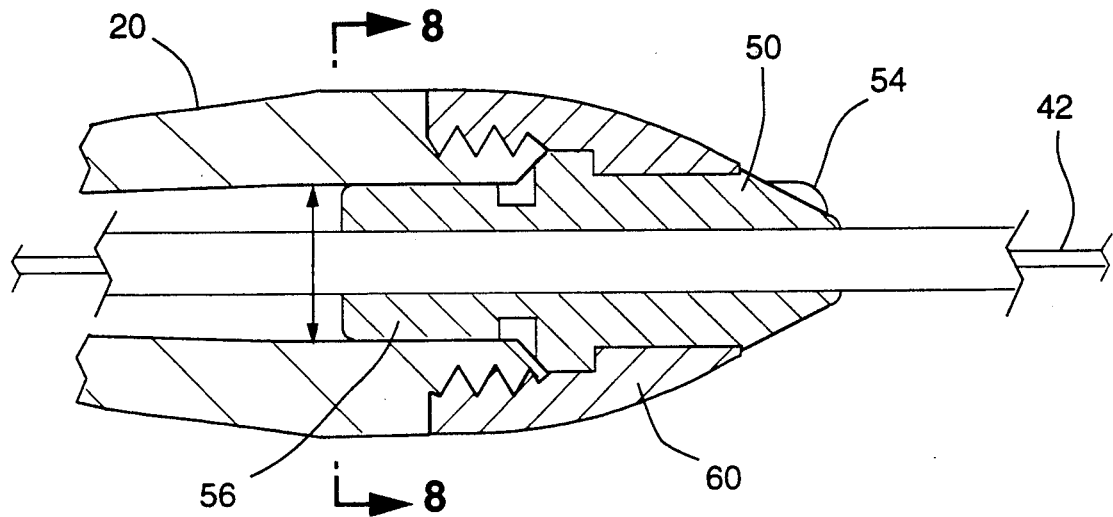
FIG. 5 is an enlarged, cross sectional view of the front end of the handpiece and tip piece.

Turning to the Figures, and in particular, FIGS. 1 to 3, the fiber optic probe 10 of the subject invention is illustrated. The probe 10 includes a handpiece 20, a tip piece 22 and a tail piece 24. When assembled, the outer surface of the probe 10 has smooth rounded contours as illustrated in FIG. 1. The outer configuration of the probe is designed for operator comfort and can be held either with a standard wrap around grip or in a pen grip.

The handpiece includes a central channel 30 extending from the front end 32 thereof to the rear end 34. In the preferred embodiment, an aluminum or stainless steel insert or sleeve 36 is formed within the handpiece to provide a more precise bore 38 for the channel 30. Preferably, the insert 36 includes a reduced diameter mating region 40 for receiving the mating ferrules as discussed below. In the proposed commercial embodiment, the inner diameter of the reduced mating region 40 is 0.1874 inches while the inner diameter of bore 38 is 0.257.

During fabrication of the handpiece, plastic is injection molded around the insert 36. In the preferred embodiment, the handpiece is formed from polysulfone plastic. As best seen in FIG. 2, the portion of the channel 30 extending from the front end 32 to the insert 36 is preferably tapered and acts as a guide for the ferrule of the tip piece 22.

Probe 10 further includes a tip piece 22. Tip piece 22 includes a central optical fiber 42 which extends the length of the tip. In the proposed commercial embodiment, the fiber 42 is formed from a low OH silica with a 440 micron core diameter. The fiber 42 is surrounded by a tubular support member 44 formed from stainless steel. Member 44 may be of any design known in the prior art and can include a straight or curved end. Examples of the types of end members 44 which could be employed are described in copending applications Ser. No. 820,303 filed Jun. 23, 1992, Ser. No. 737,694, filed Jul. 30, 1991 and Ser. No. 745,269 filed Aug. 14, 1991, all assigned to the assignee herein, the disclosures of which are incorporated by reference.

As described in the latter applications, the delivery end of the fiber is adhesively affixed within member 44. In accordance with the subject invention, and as best seen in FIG. 9, a portion of the input end of fiber 42 projects beyond the end of member 44. This portion of the fiber is snugly received within a channel 46 formed in a ferrule 48. The ferrule 48 is bonded to member 44.

This mounting arrangement provides a number of benefits. First, since the input end of the fiber is not firmly affixed, the differences in thermal expansion between the fiber and the stainless steel member are accommodated thereby permitting the tip piece to be sterilized in a steam autoclave having a large temperature cycle. In addition, by providing some amount of movement or play in the input end of the fiber, the damage which could occur if the input end is forced against the end of the fiber in the tail piece is minimized.

In a further aspect of the subject invention, the outer diameter of ferrule 48 is dimensioned to be received snugly within the narrowed diameter mating region 40 of insert 36. In the proposed commercial embodiment, the outer diameter of the ferrule 48 is 0.1872 inches.

Tip piece 22 further includes a coupler 50 for mating with the front end 32 of the handpiece. Coupler 50 preferably includes a radially projecting flag or marker 54. In the case of a delivery member 54 which projects the laser light outwardly in a direction transverse to the longitudinal axis of the member, flag 44 will be oriented on the side of the coupler opposite to the direction of propagation. In this manner, the surgeon is provided with a visual and tactile indicator of the propagation direction.

Figures 7, 8:
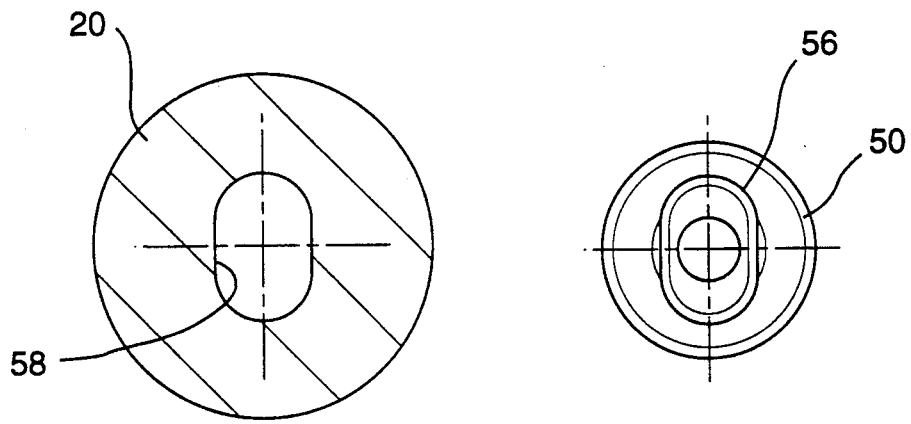
FIG. 7 is a rear elevational view of the coupler used to connect the tip piece of the probe to the handpiece.
FIG. 8 is a cross-sectional view of the channel of the handpiece taken along the line 8—8 of FIG. 5 with the tip piece removed.

It is also desirable that the direction of propagation remain constant with respect to the orientation of the handpiece. To achieve this goal, the proximal end of the coupler 50 is provided with an elliptical key 56 as best seen in FIGS. 4 and 7. Key 56 is configured to be received in a complimentary recess 58 formed in the front end of the handpiece as best seen in FIG. 8. This interlocking relationship prevents the tip piece from rotating with respect to the handpiece.

The tip piece is secured to the handpiece with a threaded nose piece 60. Nose piece surrounds coupler 50 and mates with complimentary threads 62 on the front end of the handpiece. By tightening the nose piece, the proximal end of the tip piece is drawn into the channel 30 so that the ferrule 48 is inserted into the mating region 40 of insert 36. Preferably, the nose piece 60 can be color coded to facilitate selection of the appropriate tip by the surgeon.

The tail piece 24 is connected to the rear end of the handpiece 20. Tail piece 24 includes an optical fiber 70 formed from low OH silica having a core diameter of 350 microns. It should be noted that the diameters of the fibers 42 and 70 do not have to be the same allowing for more flexibility in selecting the diameter of the end of the fiber 42 which actually delivers the laser radiation to the treatment site. It is also desirable to have the diameter of the tip fiber 42 larger than the diameter of fiber 70 to insure all of the light exiting fiber 70 is coupled into fiber 42.

Both fibers 42 and 70 are surrounded by a jacket formed from Hytrel. As is well known in the prior art, the silica fiber is typically surrounded by a glass cladding and a silicone buffer material. The delivery end of the fiber 70 is mounted within a ferrule 72. The outer configuration of ferrule 72 has the same dimensions as ferrule 48 and is therefore also tightly received within the mating region 40 of insert 36.

The optical fiber 70 is secured within the ferrule 72 with an adhesive 76. The adhesive which is selected must be capable of withstanding the heat and moisture of a steam autoclave. One suitable adhesive is an epoxy resin marketed by Epoxy Technology, Inc. under the designation Epo-Tex 353 ND.

Although the latter epoxy can itself withstand high heat, it has been found that the expansion and contraction of the sterilization cycle can cause the epoxy and fiber to separate from the ferrule. To overcome this problem, the inner surface of the ferrule is provided with a locking configuration. As best seen in FIG. 9, the locking configuration can be in the form of annular recesses or a spiral thread 78. When the epoxy is injected within the ferrule, it will occupy the voids created by the annular recesses. When cured, the outer surface of the epoxy cast will have a configuration which complements the locking configuration on the inner surface of the ferrule. This interlocking configuration will help prevent the fiber from separating from the ferrule when it is being sterilized. It should be understood that various other locking configurations could be used to achieve this goal.

As noted above, the tip piece 22 is often damaged during use and cannot be reused. However, on average, the tip piece could be used two or three times before having sufficient damage to require disposal. Therefore, in the proposed commercial embodiment, the tip piece is also formed from materials which can be sterilized in a steam autoclave. As noted above, the input end of the fiber is not adhesively secured so that it is free to expand separately from the steel member without breakage during sterilization.

Fiber 70 is threaded through a conically shaped, strain relief member 80. Strain relief member 80 can be formed from silicon. Member 80 has an axially projecting tube 82 through which the fiber 70 emerges. Mounted snugly about tube 82 is a collet 86. The front end of collet 86 is threaded 88 and is mated with similar threads 90 at the rear end of the handpiece.

Ferrule 70 is biased into abutting relationship with ferrule 48. The biasing force is created by a coil spring 94 surrounding the fiber. A spacer 96 is located between the front end of the spring and the back of the ferrule 70. As the collet 86 is tightened, the front surface of the collet functions to compress spring 94, forcing the spacer 96 into the ferrule 72 and pushing the ferrule 72 into the mating region 40 of insert 36. When the tip piece is inserted into the handpiece and tightened in place, the two ferrules are forced into contact. This tight abutment between the ferrules maximizes the coupling efficiency between the fibers.

In the preferred embodiment, the delivery end 97 of fiber 70 is spaced inwardly from the planar end surface of the ferrule. This spacing is illustrated in exaggerated form in FIG. 9. This spacing should be on the order of 50 to 100 microns. A small spacing prevents the fibers from contacting each other thereby reducing the chance of structural failure while at the same time maintaining coupling efficiency.

As noted above, the subject probe solves many of the problems associated with the prior art devices. More particularly, the probe provides for the precision optical coupling between the mating ends of the two fibers.

This coupling is located in a reduced diameter mating region, spaced from the front end of the handpiece. By this arrangement, the forces on the mated fibers, caused by the torque generated at the end of the tip piece, will be significantly less than if the mated fibers were near front of the handpiece such that optical coupling efficiency is maintained.

The amount of force experienced at the coupling is a function of the ratio between the length of the tip piece which is located within the handpiece as compared to the length of the tip piece which projects beyond the front end of the handpiece. If these two lengths were equal, the force at the coupling would be equal to the force exerted at the tip. In the proposed commercial embodiment, the length of the tip piece within the handpiece (measured from the front end of the handpiece to the input end of the fiber) is 2.4 inches while the length of the tip piece which projects beyond the front end of the handpiece is 5.0 inches. In this configuration, the force at the coupling would be about twice that experienced at the tip (5/2.4). Preferably, the ratio between the lengths of the internal and external portions of the tip piece should be no less than twenty five percent so that the forces at the coupling will not exceed four times the forces at the delivery end of the fiber.

The probe has further been designed to allow the parts to be reused by sterilization in a steam autoclave. This design obviates the need to use more time consuming and expensive gas sterilization techniques. The two part structure also allows the tip piece to be disposable.

FIG. 11 illustrates an alternate embodiment of the probe 110. The only difference from the first embodiment is that the plastic shell of the handpiece 120 is provided with slots 98 which are formed in the outer surface thereof. These slots function to reduce the time it takes for the handpiece to return to room temperature after it has been sterilized in an autoclave.

While the subject invention has been described with reference to the preferred embodiments, various changes and modifications could be made therein, by one skilled in the art, without varying from the scope and spirit of the subject invention as defined by the appended claims.

We claim:

1. A fiber optic probe comprising:
   an elongated handpiece having front and rear ends and an axial channel formed therein and extending between said ends, said channel including a mating region spaced from said front end;
   a tip piece including a first elongated optical fiber, with one end of the first fiber being mounted in a first ferrule; and
   a tail piece including a second elongated optical fiber, with one end of the second fiber being mounted in a second ferrule, and with a portion of said tip piece being mounted within said channel from the front end of the handpiece and the tail piece being mounted into said channel from the rear end of the handpiece in a manner such that the first and second ferrules are positioned within said mating region of the channel and in abutting relationship and with the portion of the tip piece extending between said one end of the fiber and the front end of the handpiece being at least twenty five percent of the length of the remaining portion of the tip piece that extends beyond the front end of the handpiece whereby efficient optical coupling between the ends of the optical fibers can be maintained as force is exerted on the tip piece during use.

2. A probe as recited in claim 1 wherein said ferrules have an outer configuration dimensioned to fit tightly within the mating region.

3. A probe as recited in claim 2 wherein the diameter of the channel is reduced in said mating region.

4. A probe as recited in claim 3 wherein said ferrules are biased into abutting relationship with a spring means.

5. A probe as recited in claim 4 wherein said spring means includes a coiled spring surrounding the second optical fiber in said tail piece and a spacer interposed between the coiled spring and the second ferrule.

6. A probe as recited in claim 5 wherein said first optical fiber is fixedly mounted in the tip piece and the position of the first ferrule within the channel is fixed by the connection of the tip piece to the handpiece.

7. A probe as recited in claim 3 wherein the diameter of said channel extending between the front end of the handpiece and the mating region is tapered.

8. A probe as recited in claim 1 wherein said end of at least one of the optical fibers is spaced inwardly from the end of the associated ferrule so that a separation is maintained between said ends of the fibers even when the ferrules are in abutting relationship.

9. A probe as recited in claim 1 wherein the end of the second optical fiber mounted in the second ferrule is secured by an adhesive.

10. A probe as recited in claim 9 wherein the inner surface of the second ferrule and the outer surface of the adhesive are provided with an interlocking configuration to prevent the adhesive and the fiber from separating from the ferrule during heating.

11. A probe as recited in claim 10 wherein the adhesive is an epoxy.

12. A probe as recited in claim 1 wherein said tip piece includes a coupler for connecting the tip piece to the front end of the handpiece and wherein one end of the coupler and said front end of the handpiece are provided with complimentary elliptical configurations to prevent the tip piece from rotating with respect to the handpiece.

13. A probe as recited in claim 1 wherein the portion of the tip piece extending between said one end of the fiber and the front end of the handpiece is about fifty percent of the length of the remaining portion of the tip piece that extends beyond the front end of the handpiece.

14. A fiber optic probe comprising:
   an elongated handpiece having front and rear ends and an axial channel formed therein and extending between said ends, said channel including a reduced diameter mating region spaced from said front end;
   a tip piece including a first elongated optical fiber, with one end of the first fiber being mounted in a first ferrule; and
   a tail piece including a second elongated optical fiber, with one end of the second fiber being mounted in a second ferrule, and with a portion of said tip piece being mounted within said channel from the front end of the handpiece and the tail piece being mounted into said channel from the rear end of the handpiece in a manner such that the first and second ferrules are positioned within said reduced diameter mating region of the channel and in abutting relationship and with said ferrules having an outer configuration dimensioned to fit tightly within the reduced diameter mating region to provide and maintain efficient optical coupling between the ends of the optical fibers as the handpiece is used.

15. A probe as recited in claim 14 wherein the portion of the tip piece extending between said one end of the fiber and the front end of the handpiece is at least twenty five percent of the length of the remaining portion of the tip piece that extends beyond the front end of the handpiece.

16. A probe as recited in claim 14 wherein the portion of the tip piece extending between said one end of the fiber and the front end of the handpiece is about fifty percent of the length of the remaining portion of the tip piece that extends beyond the front end of the handpiece.

17. A probe as recited in claim 14 wherein said ferrules are biased into abutting relationship with a spring means.

18. A probe as recited in claim 17 wherein said spring means includes a coiled spring surrounding the second optical fiber in said tail piece and a spacer interposed between the coiled spring and the second ferrule.

19. A probe as recited in claim 18 wherein said first optical fiber is fixedly mounted in the tip piece and the position of the first ferrule within the channel is fixed by the connection of the tip piece to the handpiece.

20. A probe as recited in claim 14 wherein the diameter of said channel extending between the front end of the handpiece and the mating region is tapered.

21. A probe as recited in claim 14 wherein said end of at least one of the optical fibers is spaced inwardly from the end of the associated ferrule so that a separation is maintained between said ends of the fibers even when the ferrules are in abutting relationship.

22. A probe as recited in claim 14 wherein the end of the second optical fiber mounted in the second ferrule is secured by an adhesive.

23. A probe as recited in claim 22 wherein the inner surface of the second ferrule and the outer surface of the adhesive are provided with an interlocking configuration to prevent the adhesive and the fiber from separating from the ferrule during heating.

24. A probe as recited in claim 23 wherein the adhesive is an epoxy.

25. A probe as recited in claim 14 wherein said tip piece includes a coupler for connecting the tip piece to the front end of the handpiece and wherein one end of the coupler and said front end of the handpiece are provided with complimentary elliptical configurations to prevent the tip piece from rotating with respect to the handpiece.

* * * * *